United States Patent [19]

Kreuzer et al.

[11] Patent Number: 4,620,023

[45] Date of Patent: Oct. 28, 1986

[54] METHOD FOR PREPARING HEXAMETHYLCYCLOTRISILOXANE AND USES FOR THE SAME

[75] Inventors: Franz-Heinrich Kreuzer, Martinsried; Helmut Gebauer, Munich, both of Fed. Rep. of Germany

[73] Assignee: Consortium fur Elektrochemische Industrie GmbH, Munich, Fed. Rep. of Germany

[21] Appl. No.: 524,009

[22] Filed: Aug. 17, 1983

[30] Foreign Application Priority Data

May 27, 1983 [EP] European Pat. Off. ......... 83105271.7

[51] Int. Cl.$^4$ ................................................ C07F 7/08
[52] U.S. Cl. ..................................................... 556/460
[58] Field of Search ......................................... 556/460

[56] References Cited

U.S. PATENT DOCUMENTS

| | | | |
|---|---|---|---|
| 2,860,152 | 11/1958 | Fletcher | 556/460 |
| 3,846,464 | 11/1974 | Razzano | 556/460 |
| 3,989,733 | 11/1976 | Okamoto et al. | 556/460 |
| 4,111,973 | 9/1978 | Bluestein | 556/460 |

Primary Examiner—Paul F. Shaver

[57] ABSTRACT

Hexamethylcyclotrisiloxane is prepared by heating linear, branched, or cross-linked organopolysiloxanes containing at least 50 mol percent of dimethylsiloxane units to at least 350° C. in the absence of substances which attack the siloxane group during heating and simultaneously distilling off the cyclic dimethylpolysiloxanes thus formed.

The hexamethylcyclotrisiloxane thus prepared is an excellent carrier for fragrant materials, especially where the carrier is present in admixture with other carrier substances such as tetramethylcyclobutanedione.

2 Claims, No Drawings

METHOD FOR PREPARING HEXAMETHYLCYCLOTRISILOXANE AND USES FOR THE SAME

The present invention relates to a method for preparing cyclic siloxanes, and more particularly to an improved method for preparing hexamethylcyclotrisiloxane and its use as a carrier for aromatic substances.

BACKGROUND OF THE INVENTION

A method for preparing hexamethylcyclotrisiloxane was described by Winton Patnode and Donald F. Wilcok in *The Journal of the American Chemical Society*, Vol. 68 (1946), pages 360–361, in which high molecular weight dimethylpolysiloxanes were heated to a temperature of from 350° to 400° C. The resultant condensate contained 44 percent $[(CH_3)_2SiO]_3$, 24 percent $[(CH_3)_2SiO]_4$, 9 percent $[(CH_3)_2SiO]_5$, 10 percent $[(CH_3)_2SiO]_6$ and 13 volume percent above hexamer.

Although hexamethylcyclotrisiloxane could be prepared by this method, the yield of cyclic trisiloxanes was so low that the method was not practical on a commercial scale.

Therefore, it is an object of the present invention to provide a method for preparing cyclic dimethylpolysiloxanes. Another object of this invention is to provide an improved method for preparing hexamethylcyclotrisiloxanes. Still another object of this invention is to provide an improved method for preparing higher yields of hexamethylcyclotrisiloxanes. A further object of the present invention is to provide a room air deodorizer composition containing hexamethylcyclotrisiloxane as a carrier for a fragrance substance.

SUMMARY OF THE INVENTION

The foregoing objects and others which will become apparent from the following description are accomplished in accordance with this invention, generally speaking, by providing a method for preparing hexamethylcyclotrisiloxane which comprises heating linear, branched or cross-linked organopolysiloxanes having at least 50 mol percent of dimethylsiloxane units to a temperature of at least 350° C. in the absence of materials which attack the siloxane group during heating while simultaneously distilling off the cyclic dimethylpolysiloxanes thus formed.

The resultant hexamethylcyclotrisiloxane may be used as a carrier for fragrance materials to form air freshener compositions.

DESCRIPTION OF THE INVENTION

Any linear, branched, or cross-linked organopolysiloxanes which have at least 50 mol percent of dimethylsiloxane units can be used in the method of this invention. It is preferred that the linear or essentially linear organopolysiloxanes or cross-linked organopolysiloxanes consist of at least 95 mol percent of diorganosiloxane units in which the organic groups contain at least 95 mol percent methyl groups. The other organic groups present in the organopolysiloxanes may contain in addition to the methyl groups, ethyl, vinyl, or phenyl groups or mixtures of at least two such other groups. In addition to the diorganosiloxane units, other siloxane units which may be present are triorganosiloxane, monoorganosiloxane, or $SiO_{4/2}$ units or mixtures of at least two such other units.

The organopolysiloxanes used in the method of this invention can be present in more or less pure form, but at least essentially free of substances which attack the siloxane group at 350° C. The organopolysiloxanes used in the method of this invention can also, for example, be present as organopolysiloxanes which are capable of being crosslinked, or as partially or completely crosslinked elastomers. In addition the organopolysiloxanes or elastomers may also contain the customary auxiliary substances such as fillers, pigments, cross-linking catalysts, such as organic tin compounds, or by-products of cross-linking catalysts so long as they are at least essentially free of substances which attack the siloxane group at 350° C.

It is also possible to use not only one type of organopolysiloxane, but also mixtures of various types of organopolysiloxanes in the method of this invention. It is preferred that the organopolysiloxanes be heated to a maximum temperature of about 800° C.

Substances which do not attack the siloxane group, that is a group having the following formula

and thus lead to rearrangement, polymerization, or depolymerization of organopolysiloxanes at temperatures of at least 350° C., are tin oxides which are formed from organic tin compounds, However, at 500° C., for example, the alkali content of ordinary soft soda glass, for example, probably does attack the siloxane group. The presence of substances which attack the siloxane group, then, is to be avoided in accordance with this invention. Thus, not only the organopolysiloxanes used in accordance with the invention, but also the apparatus used in the method of this invention, especially where the surface is heated to a temperature of at least 350° C., must be free of substances, to the extent possible, which attack the siloxane group at 350° C.

Preferably, the heating of linear, branched, or cross-linked organopolysiloxanes having at least 50 mol percent of dimethylsiloxane units to at least 350° C. is carried out in vessels made of iron or steel, copper, nickel, or chromium or alkali-free alloys of these metals.

During the heating of the organopolysiloxanes to at least 350° C., a gas which is inert with respect to the organopolysiloxanes, such as nitrogen, can be passed through the organopolysiloxanes.

The method of this invention is preferably carried out at atmospheric pressure, that is, at 1 bar or approximately 1 bar; however, elevated or reduced pressures can also be used, if desired.

Heating of linear, branched, or cross-linked organopolysiloxanes which consist of at least 50 mol percent of dimethylsiloxane units, can take place at least at 350° C. with rotation or agitation. The method of this invention can be carried out in a batch or in a semicontinuous or continuous manner.

The hexamethylcyclotrisiloxane prepared in accordance with this invention is an excellent carrier substance for aromatic or fragrance producing substances, where the carrier substance may be present in admixture with other carrier substances such as tetramethylcyclobutanedione.

All parts and percentages in the following examples are by weight unless otherwise specified.

The V4A steel mentioned in the following examples consists of 18 weight percent chromium, 11 weight percent nickel, 2 weight percent molybdenum, 0.07 weight percent carbon, with the balance being iron.

EXAMPLE 1 AND COMPARISON EXPERIMENTS (a) THROUGH (d)

Nitrogen at a rate of 160 ml per minute (measured at standard conditions) and a dimethylpolysiloxane at a rate of 510 ml per hour, having an Si-bonded hydroxyl group in each of its terminal units and having a viscosity of 100 mPa.s at 25° C. were introduced simultaneously into a vessel made of V4A steel having an inside diameter of 90 mm and a height of 180 mm and heated electrically to 600° C. The cyclic diorganopolysiloxanes formed during heating were continuously distilled off and condensed in descending condensers attached to the vessel.

In the comparison examples, the vessel in which organopolysiloxane is heated contains 0.5g of a siloxane group-attacking alkali compound in addition to the organopolysiloxane and nitrogen, as indicated in Table I.

The following results are obtained:

| Cyclic Dimethylpolysiloxanes | |
|---|---|
| Number of Siloxane Units | Percent of Cyclic Dimethylpolysiloxanes |
| 3 | 73.5 |
| 4 | 16.2 |
| 5 | 2.2 |
| 6 | 1 |
| 7 | 1 |

The weight ratio of trisiloxane to tetrasiloxane is 4.54.

EXAMPLES 3 THROUGH 7

The procedure described for Example 1 is repeated except for the following modifications:

I. Between the reaction vessel containing the heated organopolysiloxane and the descending condenser, a jacketed metal tube is inserted which is heated to 135° C. The descending condenser is maintained at 80° C.

II. The rate of addition of the nitrogen is 250 ml/min instead of 160 ml/min (measured at standard conditions).

TABLE I

| | Alkali Compound | Percentage of Cyclic Dimethylpolysiloxanes having the following number of siloxane units | | | | | | Trisiloxane/tetrasiloxane Weight Ratio |
|---|---|---|---|---|---|---|---|---|
| | | 3 | 4 | 5 | 6 | 7 | 8 | |
| Examples | | | | | | | | |
| 1 | — | 65.8 | 26.2 | 5.0 | 1.4 | 1.1 | 0.5 | 2.51 |
| Comparison Examples | | | | | | | | |
| (a) | Li$_2$CO$_3$ | 49.6 | 22.4 | 11.2 | 12.9 | 2.8 | 0.8 | 2.21 |
| (b) | Na$_a$CO$_3$ | 33.0 | 22.5 | 11.4 | 23.0 | 7.8 | 2.0 | 1.47 |
| (c) | K$_2$CO$_3$ | 30.0 | 32.1 | 14.0 | 13.4 | 8.1 | 2.4 | 0.93 |
| (d) | Cs$_2$CO$_3$ | 20.9 | 51.2 | 20.3 | 6.3 | 1.3 | | 0.40 |

EXAMPLE 2

A cross-linked organopolysiloxane was prepared by mixing 100 parts of a dimethylpolysiloxane having an Si-bonded hydroxyl group in each of its terminal units and a viscosity of 500 mPa.s at 25° C. with 3 parts of ethyl polysilicate having an SiO$_2$ content of 40 percent and 1 part dibutyltin diacylate in which the acylate groups are derived from a mixture of carboxylic acids having 9 to 11 carbon atoms per molecule in which the carboxyl group in at least 90 percent of the acids is bonded to a tertiary carbon atom (a so-called "dibutyl-tin diversatate"). The material is poured into a mold and allowed to cross-link at room temperature.

After 8 days the organopolysiloxane elastomer thus prepared is heated to 500° C. in the apparatus described in Example 1. The following result is obtained:

III. In Example 3, the viscosity of the dimethylpolysiloxane is 100 mPa.s at 25° C. and in Examples 4 through 7, the viscosity of the dimethylpolysiloxane is 600 mPa.s at 25° C.

IV. The rate of addition of the dimethylpolysiloxane is shown in Table II.

V. The temperature at which the dimethylpolysiloxane is heated is shown in Table II.

TABLE II

| Example | Temperature* °C. | Dimethylpolysiloxane ml/hr | Percentage of Cyclic Dimethylpolysiloxane having the following number of siloxane units | | | Trisiloxane/tetrasiloxane Weight/ratio |
|---|---|---|---|---|---|---|
| | | | 3 | 4 | 5 to 8 | |
| 3 | 600 | 960 | 72.3 | 23.4 | 4.3 | 3.09 |
| 4 | 600 | 360 | 77.8 | 22.2 | 0.1 | 3.52 |
| 5 | 600 | 720 | 78.1 | 21.7 | 0.6 | 3.60 |
| 6 | 515 | 1080 | 80.5 | 18.0 | 1.5 | 4.47 |
| 7 | 505 | 1800 | 78.7 | 18.0 | 3.3 | 4.37 |

*Temperature at which the organopolysiloxane is heated.

COMPARISON EXAMPLES (e) THROUGH (g)

About 500 g of a dimethylpolysiloxane having an Si-bonded hydroxyl group in each of its terminal units and having a viscosity of 500 mPa.s at 25° C., together with the additives shown in Table III, are heated in a one liter glass reactor to the temperatures indicated. The cyclic dimethylpolysiloxanes are distilled off via a packed column which is approximately 200 mm in length.

TABLE III

| Comparison Example | Temperature °C. | Additive | Percentage of Cyclic Dimethylpolysiloxane having the following number of siloxane units | | | | | | Trisiloxane/tetrasiloxane Weight/Ratio |
|---|---|---|---|---|---|---|---|---|---|
| | | | 3 | 4 | 5 | 6 | 7 | 8 | |
| (e) | 150 | 15 g KOH | 3.6 | 92.3 | 4.1 | | | | 0.04 |
| (f) | 150 | 5 g para-toluene-sulfonic acid | 0.5 | 65.9 | 20.0 | 11.0 | 1.9 | 0.7 | 0.01 |
| (g) | 500 | — | 38.7 | 17.8 | 9.1 | 21.5 | 10.5 | 2.27 | 2.17 |

EXAMPLE 8

About 20 g of the hexamethylcyclotrisiloxane prepared in accordance with Example 1 are pulverized and thoroughly blended with 2 g of perfume oil ("Sea Breeze", Dragoco) and then pressed in a mold to form a cylinder. The cylinder obtained in this manner is placed in a plastic container having several small openings. The contents of the plastic container are effective as a room air deodorizer until they have completely volatilized over a period of about 25 days.

EXAMPLE 9

About 20 g of the hexamethylcyclotrisiloxane prepared in accordance with Example 2 are pulverized and thoroughly blended at 60° C. with 2 g of orange terpenes. The melt thus obtained is allowed to solidify in a cylinderical mold. The cylinder thus obtained is placed in a plastic container having several small openings. The contents of the plastic container remain effective as a room air deodorizer until they have completely volatilized over a period of about 25 days.

EXAMPLE 10

About 18 g of the hexamethylcyclotrisiloxane prepared in accordance with Example 3 are pulverized and thoroughly blended with 12 g "Lilac" perfume oil whose composition is shown below and 1 g of pyrogenic silica having a surface area of about 200 m²/g at 60° C. and the melt thus obtained is allowed to solidify in a polystyrene petri dish having 5 longitudinal slots in its cover. The contents of the petri dish give off a pleasant odor for 28 days in a room of 45 m³.

| Composition of the "Lilac" perfume oil | |
|---|---|
| 18.0 percent hydroxycitronellal | 0.5 percent phenylacetaldehyde |
| 1.7 percent cinnamyl alcohol | 6.0 percent anisaldehyde |
| 8.0 percent terpineol | 16.0 percent piperonal |
| 18.0 percent benzyl alcohol | 2.5 percent indole (10%) |
| 20.0 percent phenylethyl alcohol | 7.3 percent jasmine base |

| -continued | |
|---|---|
| Composition of the "Lilac" perfume oil | |
| 2.0 percent linalool | |

EXAMPLE 11

A mixture containing 10 g of pulverized hexamethylcyclotrisiloxane prepared in accordance with Example 4, 30 g of tetramethylcyclobutanedione, and 5 g of a lily of the valley composition whose composition is shown below is pressed into a cube. The cube is hung freely in a room and remains effective as a room air deodorizer until it has been completely volatilized over a period of about 23 days.

| Lily of the valley composition | |
|---|---|
| | Parts |
| hydroxycitronellal | 50 |
| alpha-hexylcinnamaldehyde | 4 |
| benzyl alcohol | 4 |
| geraniol | 3 |
| citronellol | 3 |
| linalool | 3 |
| citronellal | 3 |
| linalyl acetate | 2 |
| indole (10 percent) | 1 |
| cis-3-hexenol (10 percent) | 1 |
| lauryl aldehyde (10 percent) | 1 |

What is claimed is:

1. An improved method for preparing hexamethylcyclotrisiloxane by heating linear, branched, or crosslinked organopolysiloxanes having at least 50 mol percent of dimethylpolysiloxane units to at least 320° C. and simultaneously distilling off the cyclic dimethylpolysiloxanes formed during heating, the improvement which comprises heating the organopolysiloxanes in the absence of acidic and basic compounds which attack the siloxanes group.

2. The improved method of claim 1, in which the organopolysiloxane is heated to at least 350° C. in a vessel made of iron or steel, copper, nickel, or chronium or alkali-free alloys of these metals.

* * * * *